United States Patent [19]

Kyogoku et al.

[11] Patent Number: 5,270,446
[45] Date of Patent: Dec. 14, 1993

[54] DECOLORIZED CROSSLINKED PRODUCTS AND METHOD FOR DECOLORIZATION OF CROSSLINKED PRODUCTS

[75] Inventors: Nobuo Kyogoku; Keiko Harada, both of Osaka, Japan

[73] Assignee: Suntory Limited, Osaka, Japan

[21] Appl. No.: 884,884

[22] Filed: May 18, 1992

Related U.S. Application Data

[63] Continuation of Ser. No. 503,990, Apr. 4, 1990, abandoned.

[30] Foreign Application Priority Data

Apr. 4, 1989 [JP] Japan ................................. 1-85395

[51] Int. Cl.$^5$ ...................... A61K 37/02; C08B 37/08
[52] U.S. Cl. ................................. 530/300; 530/378; 530/356; 530/354; 536/20; 536/55.3; 536/127; 426/656; 426/657; 426/658; 426/573; 426/601
[58] Field of Search ................... 536/20, 17.9, 18.7, 536/55.3, 127; 530/300, 378, 356, 354; 426/573, 656, 658, 657, 601; 435/174

[56] References Cited

U.S. PATENT DOCUMENTS

| | | | |
|---|---|---|---|
| 4,232,159 | 11/1980 | Touyama et al. | 546/112 |
| 4,247,698 | 1/1981 | Toyama et al. | 536/18.1 |
| 4,347,356 | 8/1982 | Touyama et al. | 546/112 |
| 4,401,825 | 8/1983 | Weinges et al. | 560/121 |
| 4,762,918 | 8/1988 | McDaniel et al. | 536/127 |
| 4,878,921 | 11/1989 | Koga et al. | 8/646 |
| 4,983,524 | 1/1991 | Fujikawa et al. | 435/174 |
| 5,037,664 | 8/1991 | Kyogoku et al. | 530/408 |
| 5,098,733 | 3/1992 | Kyogoku et al. | 530/378 |

FOREIGN PATENT DOCUMENTS

| | | |
|---|---|---|
| 2013706 | 4/1990 | Canada . |
| 306650 | 3/1989 | European Pat. Off. . |
| 306651 | 3/1989 | European Pat. Off. . |

OTHER PUBLICATIONS

Fujikawa et al, Genipin, A New Type of Protein Crosslinking Reagent from Gardenia Fruits, Agricultural and Biological Chemistry, The Agricultural Chemical Society of Japan, vol. 52, Mar. 1988, pp. 869–870.

*Primary Examiner*—Johnnie R. Brown
*Assistant Examiner*—Everett White
*Attorney, Agent, or Firm*—Cushman, Darby & Cushman

[57] ABSTRACT

A crosslinked product of a primary amino group-containing compound such as proteins, chitosan or a mixture thereof is disclosed. The product has a crosslinked structure formed by crosslinking with an iridoid compound, and the blue color developed by the crosslinking is decolorized. Also, a method for decolorization of the above crosslinked product is disclosed. The method comprises reacting a crosslinked product obtained by crosslinking a primary amino group-containing compound with an iridoid compound, with at least one decolorizing agent selected from the group consisting of an oxidizing agent, a reducing agent and a reductone. The decolorized product and the method for decolorization according to the present invention can be broadly applied in the fields of foodstuffs, cosmetics, pharmaceuticals and the like where blue tone coloration is undesirable.

11 Claims, No Drawings

DECOLORIZED CROSSLINKED PRODUCTS AND METHOD FOR DECOLORIZATION OF CROSSLINKED PRODUCTS

This is a continuation of application No. 07/503,990 filed on Apr. 4, 1990, now abandoned.

FIELD OF THE INVENTION

This invention relates to a method for decolorization of a crosslinked product obtained by reacting a primary amino group-containing compound with an iridoid compound and also to a decolorized product.

BACKGROUND OF THE INVENTION

It is known that the iridoid compound derived from the gardenia fruit reacts with a primary amino group-containing compound and, upon oxidation polymerization of the resulting reaction product, a blue color dye is produced, as disclosed in Japanese Patent Publication No. 57-14781 and Japanese Patent Unexamined Publication (Kokai) No. 63-47167. Also, Japanese Patent Unexamined Publication (Kokai) No. 63-157981 discloses that the iridoid compound reacts to form crosslinks between proteins or between an enzyme protein and an amino group-containing carrier and, upon oxidation polymerization, it forms a stable crosslinking structure. Further, the above-described ability to form a crosslinking structure can be utilized for improving the physical properties of primary amino group-containing compounds such as proteins, for example, heat-resistance, water-resistance, acid-resistance, and also is expected to have a wide variety of applications.

However, the crosslinked product obtained by using the iridoid compound has a blue color due to its chemical structure, thus limiting its applications. For example, the blue color produced in crosslinked products precludes their use in most foodstuffs, because types and quantities of foods having a cold color, in particular, a blue color, are relatively small.

Thus, it has long been desired to develop a method for decolorizing the blue color dye produced by crosslinking a primary amino group-containing compound such as proteins with an iridoid compound, for example, genipine, while maintaining the crosslinked structure of the resulting crosslinked primary amino group-containing compound.

As a result of extensive studies, the present inventors found that the blue color can be decolorized by treating the crosslinked product obtained with an iridoid compound, for example, genipine with an oxidizing agent, a reducing agent or a reductone such as ascorbic acid (or isoascorbic acid), and on that basis completed the present invention.

SUMMARY OF THE INVENTION

An object of the present invention is to provide a decolorized crosslinked product of a primary amino group-containing compound.

Another object of the present invention is to provide a method for decolorization of the crosslinked product of a primary amino group-containing compound.

The above and other objects of the present invention can be achieved by a method for decolorization of a crosslinked product which comprises reacting a crosslinked product which is obtained by crosslinking a primary amino group-containing compound with an iridoid compound, with at least one decolorizing agent selected from the group consisting of an oxidizing agent, a reducing agent and a reductone; and a crosslinked product of a primary amino group-containing compound having a crosslinked structure formed by crosslinking with an iridoid compound in which the blue color produced by the crosslinking has been decolorized.

DETAILED DESCRIPTION OF THE INVENTION

The term "decolorization" as used herein means not only decolorization of the blue color produced by crosslinking reaction of the iridoid compound, but also discoloration or color change of the blue color into different colors, for example, brown or yellow.

The iridoid compounds which can be used in the present invention are not limited to any specific compounds as long as they possess the ability to crosslink a primary amino group-containing compound, and include, for example, aglycones such as geniposide, gardenodide and geniposidic acid. Of these compounds, genipine which is an aglycone of geniposide and which is derived from the fruit of gardenia is most preferred. These iridoid compounds can be prepared by the procedure as described in Japanese Patent Publication No. 57-14781 and Japanese Patent Unexamined Publication (Kokai) No. 61-47167.

The primary amino group-containing compounds which can be used in the present invention include a wide variety of compounds which are capable of forming blue colored cross-linked products upon reaction with the above-described iridoid compounds, and, in particular, proteins and chitosan can be effectively used. The proteins are not limited by origin and can consist of any vegetable proteins, animal proteins, or proteins of a microbial origin. The vegetable proteins include defatted materials of oil-stuff seeds (defatted soybean) or proteins isolated from soybean or defatted soybean. Examples of animal proteins include milk protein, egg protein, collagen, gelatin, etc.

In using the primary amino group-containing compounds, these compounds may be crosslinked not only between the same type of compounds, but also between different types of compounds. For example, compounds to be crosslinked may be a mixture of two or more of proteins, chitosan and other primary amino group-containing compounds. Also, the compounds may be an emulsion comprising a primary amino group-containing compound such as proteins and oils or fats.

Further, the crosslinked product is not limited to any specific shape and can be in the form of capsules, mass, sheet, filament, particle, etc. These shaped materials can be formed by pouring the primary amino group-containing compound into a mold having a desired shape such as a sheet or mass, and performing crosslinking in the mold. For example, a sheet can be prepared by immersing a primary amino group-containing compound which has previously been gelled in a sheet form by a method other than crosslinking with an iridoid compound into a solution of an iridoid compound, or by adding an iridoid compound to a solution of the primary amino group-containing compound such as a protein, and pouring the mixture into a mold in the desired thickness, followed by reacting while being subjected to heating in dryer.

According to the method of the present invention, a decolorizing agent selected from oxidizing agents, reducing agents, or reductones such as ascorbic acid or isoascorbic acid can be added previously to a primary amino group-containing compound such as proteins, an iridoid compound or both of these compounds prior to the crosslinking, and the decolorization reaction may be effected simultaneously with the crosslinking reaction. Alternatively, the crosslinked product obtained after the crosslinking reaction may be immersed in a solution of a decolorizing agent. When the oxidizing agent is in a gaseous state, the decolorization can be effected by placing the crosslinked product in an atmosphere of the oxidizing agent or bubbling the gaseous oxidizing agent into water in which the crosslinked product has been immersed.

Oxidizing agents which can be used in the present invention include hydrogen peroxide, oxyacids or salts thereof (such as sodium chlorite, potassium bromate, ammonium persulfate, sodium hypochlorite, bleaching powder), chlorine dioxide, halogen (such as chlorine, bromine), dehydroascorbic acid, ozone, etc. However, other oxidizing agents can also be used in the present invention as long as they can attain the objects of the present invention.

The reductones which can be used in the present invention include ascorbic acid, isoascorbic acid, triosereductone, enaminol, thiolenol, endiamine, etc. Of these compounds, ascorbic acid and isoascorbic acid are preferred.

Ascorbic acid and isoascorbic acid possess an activity for decolorizing a blue color under a pH condition below neutral. This is considered to be due to the oxidizing activity of dehydroascorbic acid, or a steric isomer thereof, i.e. dehydroisoascorbic acid, produced from ascorbic acid or isoascorbic acid. Accordingly, an ascorbate oxidase which has a function for converting ascorbic acid into dehydroascorbic acid can be used in combination.

When a chlorine-containing oxidizing agent such as sodium hypochlorite, bleaching power, etc. is used, it is preferable to treat the crosslinked product with a reducing agent such as hydrosulfite, potassium pyrosulfite, or with an acid such as hydrochloric acid in order to remove any remaining chlorine after the decolorization treatment. Examples of the reducing agent which can be used for this purpose include hydrosulfite, sodium hydrogen pyrosulfite, sodium sulfite, potassium pyrosulfite, etc.

The above reducing agents also effect a certain degree of decolorization, but a better decolorization effect can be obtained by using an oxidizing agent rather than the reducing agent. The oxidizing agent, the reducing agent or the reductones such as ascorbic acid or isoascorbic acid as decolorizating agents can be used alone or in a combination of two or more thereof. For example, the decolorization effect of the reductones such as ascorbic acid can be increased by using the reductone with oxygen, hydrogen peroxide or a metal ion such as iron.

Although the mechanism whereby decolorization of the crosslinked product is brought about is not clear, it is surprised that double bonds which participate in the coloration among the chemical structures similar to blue coloring substances produced by crosslinking are oxidized or reduced by the treatment with an oxidizing agent, a reducing agent or a reductone.

The iridoid compound for crosslinking of the primary amino group-containing compound is generally used in a proportion of from 0.001 to 1.0 part by weight per part by weight of the primary amino group-containing compound on a dry basis.

On the other hand, the oxidizing agent, the reducing agent or the reductone such as ascorbic acid or isoascorbic acid is generally used in a proportion of from 0.01 to 3 parts by weight per part of the primary amino group-containing compound on a dry basis, though the proportion varies depending upon the type of the decolorizing agent used. When the decolorizing agent is used in a proportion below 0.01 part by weight, a satisfactory decolorizing effect cannot be obtained. On the other hand, when the decolorizing agent is used at a proportion higher than 3 parts by weight, it may adversely affect the properties of the primary amino group-containing compound. In particular, proteins are undesirably denatured by oxidation of the decolorizing agent.

The decolorization treatment can usually be effected at a pH of from 2 to 10, at a temperature of from 5° to 70° C. for a treating time of from about 10 minutes to about 70 hours, though the treatment time varies depending upon the pH and reaction temperature conditions used, as well as the types of decolorizing agent, iridoid crosslinking agent and primary amino group-containing compounds used. According to the embodiment used in the treatment, the crosslinked product can be allowed to stand in an immersed state in a solution of a decolorizing agent, or can be treated in the solution while being stirred or shaken. Further, in the case where the decolorizing agent is blended with the crosslinking agent or the primary amino group-containing compound so as to effect decolorization simultaneously with crosslinking, decolorization can be effected under the above conditions and also under conditions used for crosslinking.

The decolorization method and the decolorized crosslinked product according to the present invention can be used not only for foodstuffs but also in a wide variety of fields such as in pharmaceuticals and cosmetics.

The present invention is further illustrated by the following examples and test example, but the present invention is not limited thereto.

TEST EXAMPLE 1

$\beta$-Lactoglobulin (0.3 mM) and genipine (9 mM) were dissolved in a phosphate buffer solution (pH 7) and a crosslinking reaction was effected for 5 hours at 40° C. After the crosslinking, hydrogen peroxide was added to the reaction solution at a $H_2O_2$ concentration of 3% in the solution. The resulting mixture was adjusted to a pH of 9, and decolorization was conducted for 1 hour at 40° C. An uncrosslinked sample, a crosslinked sample and a sample obtained by crosslinking and then decolorization with $H_2O_2$ were then tested for the absorbance and the SDS electrophoresis (concentrated gel, 3%, and separated gel, 12.5%).

As a result, the crosslinked sample showed absorbance at a wavelength near 600 nm due to the blue color which was not observed in the uncrosslinked sample. However, the absorbance near 600 nm disappeared in the crosslinked and decolorized sample.

On the other hand, in the SDS electrophoresis test, the crosslinked sample and the crosslinked and decolorized sample did not show a band corresponding to uncrosslinked $\beta$-lactoglobulin (molecular weight: about 18,400) but a band corresponding to molecular weights more than 200,000 existed.

The above results clearly show that, according to the method of this invention, the blue color of the crosslinked product is completely decolorized and that the crosslinking structure is retained even after the decolorization treatment.

TEST EXAMPLE 2

20 g of gelatin was swelled in 80 g of water and dissolved therein by warming at 70° C., and 0.1 g of genipine was added to the solution. The mixture was coated at a thickness of 1 mm in a mold frame and crosslinked for 1 hour in a dryer at 70° C. The resulting gel-like film of gelatin was immersed in a 5% aqueous solution of hydrogen peroxide (pH 9) for 30 minutes to effect the decolorization treatment.

The color of the film was determined by the color difference meter NDJ-1001DP (manufactured by Nippon Denshoku Kogyo Kabushiki Kaisha) using a cell for measurement of solid materials.

Also, the film was cut into square of 10×10 mm and put into a test tube with 20 ml of distilled water. The temperature of the content in the test tube was elevated at a rate of 1° C. per minute so as to determine a temperature at which the film sample was dissolved in water.

Separately, 20 g of gelatin was swelled in 80 g of water and then dissolved therein by warming at 70° C. to prepare a gelatin solution. The solution was then coated at a thickness of 1 mm in a mold frame and solidified by cooling to prepare a film which was used as a control.

The test results obtained are shown in Table 1 below.

TABLE 1

| Film Sample | Measured Values | | | Dissolving Temperature (°C.) |
| --- | --- | --- | --- | --- |
| | L | a | b | |
| A | 16.42 | −0.54 | 0.37 | 46 |
| B | 7.36 | −0.79 | 0.95 | 100 or higher |
| C | 15.78 | −0.50 | 0.33 | 100 or higher |

A: Uncrosslinked gelatin film
B: Crosslinked gelatin film
C: Crosslinked and subsequently decolorized gelatin film The above test results show that the color of the gelatin sample C crosslinked with genipine returned to that of the uncrosslinked gelatin sample A by decolorization with hydrogen peroxide while retaining the heat-resistance property produced by crosslinking.

EXAMPLE 1

0.1 g of the oxidizing agent (potassium bromate or ammonium persulfate), ascorbic acid or isoascorbic acid was added to 15 g of acid-treated gelatin and 0.1 g of genipine, and a citrate buffer solution (pH 4) was added to the mixture to make the total weight 100 g. The resulting mixture was allowed to stand at 30° C. for 2 hours to effect the cross-linking reaction. The resulting gelled gelatin showed an improved heat-stability to a degree that it did not dissolve upon heating at 50° C. The colors developed in the cross-linked gelatins which vary depending upon the type of the decolorizing agent used, such as the oxidizing agent, are shown in Table 2 below. In Table 2, a crosslinked gelatin sample using no decolorizing agent is shown as a control.

TABLE 2

| Decolorizing Agent | Color Tone of Crosslinked Gelatin |
| --- | --- |
| Potassium bromate | Brown |
| Ammonium persulfate | Brown |
| Ascorbic acid | Dark brown |
| Isoascorbic acid | Dark brown |
| Control | Deep blue |

EXAMPLE 2

3 g of alkali-treated gelatin and 0.03 g of genipine were dissolved in distilled water to make the total weight of the solution 30 g. This solution was dropped from a nozzle into a cooled oil to form gelled spherical globules each having a diameter of about 3 mm. The resulting spherical gloubules were allowed to stand at 20° C. for 15 hours to effect crosslinking. After removing the oil, the crosslinked spherical gells were immersed in a gas-cleaning bottle containing 1 liter of distilled water, and ozone gas was bubbled into the distilled water through a tube equipped on the bottle at a rate of 1.5 g per hour, using an ozonizer (OS-1N Model, manufactured by Mitsubishi Denki Kabushiki Kaisha).

As a result, all the spherical gells were completely decolorized after 10 minutes and further did not dissolve even when they were placed in a water bath at 60° C., indicating that the heat-stability produced by the crosslinking was maintained after the decolorization treatment.

EXAMPLE 3

Chitosan was added to a 10 wt % aqueous solution of citric acid to prepare a 2 wt % aqueous solution of chitosan. 0.1 g of genipine was dissolved in the solution, and the resulting solution was coated in a mold frame to form a film having a thickness of 800 microns. The film was dried in a dryer at 80° C. for 1 hour to obtain a gelled film of chitosan. The film was then immersed in a 5% aqueous solution of hydrogen peroxide which had been adjusted to a pH of 9 for 30 minutes at room temperature to effect the decolorization.

The resulting film of chitosan was transparent, plastic and showed heat-resistance to such a degree that it did not dissolve in hot water at 100° C.

EXAMPLE 4

10 g of collagen (MCP-1, produced by Miyagi Chemical Industries Co., Ltd.) was blended with 90 ml of a 1.5% citric acid aqueous solution and dissolved therein. The resulting solution was adjusted to a pH of 3 with 10% citric acid, and the mixture was coated in a mold frame to form a film having a thickness of 700 microns. Then, the film was contacted with a coagulating solution which was a saturated sodium chloride solution adjusted to a pH of 10 to effect the gelation of the film. The gelled collagen film was immersed in a 0.5 wt % aqueous solution of genipine (pH 10) at room temperature for 1 day to effect the crosslinking reaction. Then, the resulting crosslinked film was immersed in a 5% hydrogen peroxide aqueous solution which had been adjusted to a pH of 10 at room temperature for 30 minutes to effect the decolorization.

The collagen film thus obtained was white, plastic and did not dissolve in hot water at 100° C.

EXAMPLE 5

9 g of orange oil was added to 30 g of a 10 wt % aqueous solution of acid-treated gelatin at 40° C., and the mixture was emulsified by stirring to form an oil-in-water emulsion. To the resulting emulsion was added 30 g of a 10% aqueous solution of gum arabic preheated at 40° C., and the mixture was blended. Then, 140 g of water warmed at 40° C. was added to the mixture, and the mixture was adjusted to a pH of 4.0 with citric acid.

The mixture was quenched to 10° C. while stirring, and 3 g of genipine was added thereto. The mixture was gently stirred at 20° C. for 18 hours to effect hardening to obtain microcapsules comprising the capsule wall of gelatin and the orange oil encapsulated therein.

The microcapsules were separated from water, and 5 g of the microcapsules was added to 20 ml of an aqueous solution of sodium hypochlorite. The mixture was stirred at room temperature for 1 hour to effect the decolorization and washed with water.

The resulting microcapsules had a white color and did not dissolve when they were dispersed in hot water at 100° C.

As described in the above examples, in accordance with the method of this invention, the blue color produced in crosslinked products formed by crosslinking a primary amino group-containing compound such as proteins, chitosan, etc. with an iridoid compound, in particular, genipine, can be effectively decolorized without adversely affecting the crosslinked structure. By decolorization of the blue color, the crosslinked product is expected to have a wide range of applications as described above.

What is claimed is:

1. A crosslinked product decolorized of blue color formed during crosslinking of a primary amino group-containing compound with an iridoid compound;
    said primary amino group-containing compound being selected from the group consisting of proteins isolated from oil seeds, proteins isolated from soybean, milk protein, egg protein, collagen, gelatin, chitosan and a mixture thereof; and
    said iridoid compound being a substance selected from the group consisting of genipin, geniposide, gardenoside, geniposidic acid and a mixture thereof.

2. A crosslinked product of a primary amino group-containing compound as claimed in claim 1, wherein said crosslinked structure is formed by crosslinking with said iridoid compound at a proportion of from 0.001 to 1.0 part by weight per part by weight of the primary amino group-containing compound.

3. A crosslinked product of a primary amino group-containing compound as claimed in claim 1, wherein said iridoid compound is genipine.

4. A crosslinked product of a primary amino group-containing compound as claimed in claim 3, wherein said genipine is used for crosslinking at a proportion of from 0.001 to 0.1 part by weight per part by weight of the primary amino group-containing compound.

5. A method for decolorization of a crosslinked product which comprises the steps of:
    a) contacting a crosslinked product obtained by crosslinking a primary amino group-containing compound with an iridoid compound, with a decolorizing agent, wherein said decolorizing agent is a material selected from the group consisting of an oxidizing agent, a reducing agent and a reductone, and
    b) recovering a decolorized product,
        said primary amino group-containing compound being selected from the group consisting of proteins isolated from oil seeds, proteins isolated from soybean, milk protein, egg protein, collagen, gelatin, chitosan and a mixture thereof; and
        said iridoid compound being a substance selected from the group consisting of genipin, geniposide gardenoside, geniposidic acid and a mixture thereof.

6. A method for decolorization of a crosslinked product as claimed in claim 5, wherein said crosslinked structure is formed by crosslinking with said iridoid compound at a proportion of from 0.001 to 1.0 part by weight per part by weight of the primary amino group-containing compound.

7. A method for decolorization of a crosslinked product as claimed in claim 5, wherein said decolorizing agent is used at a proportion of from 0.01 to 3 parts by weight of the crosslinked product.

8. A method for decolorization of a crosslinked product as claimed in claim 5, wherein said oxidizing agent is a material selected from the group consisting of hydrogen peroxide, oxyacids, sodium chlorite, potassium bromate, ammonium persulfate, sodium hypochlorite, bleaching powder, chlorine dioxide, halogen, dehydroascorbic acid, and ozone.

9. A method for decolorization of a crosslinked product as claimed in claim 5, wherein said reducing agent is a material selected from the group consisting of hydrosulfite, sodium hydrogen pyrosulfite, sodium sulfite, and potassium pyrosulfite.

10. A method for decolorization of a crosslinked product as claimed in claim 5, wherein said reductone is a material selected from the group consisting of ascorbic acid, isoascorbic acid, triosereductone, enaminol, thiolenol, and endiamine.

11. A method for decolorization of a crosslinked product as claimed in claim 5, wherein said decolorizing agent is a material selected from the group consisting of
    a mixture of an oxidizing agent and a reductone and
    a mixture of a reducing agent and a reductone.

* * * * *